(12) United States Patent
Beran et al.

(10) Patent No.: US 8,460,627 B2
(45) Date of Patent: Jun. 11, 2013

(54) APPARATUS AND PROCESS FOR DECOMPOSING DINITROGEN MONOXIDE IN AN ADIABATIC FIXED BED REACTOR

(75) Inventors: Franz Beran, Munich (DE); Karl-Heinz Hofmann, Germering (DE); Nicole Schödel, München (DE); Wolfgang Schmehl, Hamburg (DE); Ulrike Wenning, Pullach (DE); Hans-Jörg Zander, München (DE)

(73) Assignee: Linde Aktiengesellschaft, München (DE)

( * ) Notice: Subject to any disclaimer, the term of this patent is extended or adjusted under 35 U.S.C. 154(b) by 0 days.

(21) Appl. No.: 13/144,224

(22) PCT Filed: Jan. 5, 2010

(86) PCT No.: PCT/EP2010/000013
§ 371 (c)(1),
(2), (4) Date: Sep. 21, 2011

(87) PCT Pub. No.: WO2010/081642
PCT Pub. Date: Jul. 22, 2010

(65) Prior Publication Data
US 2012/0014855 A1    Jan. 19, 2012

(30) Foreign Application Priority Data
Jan. 13, 2009   (DE) .......................... 10 2009 004 431

(51) Int. Cl.
*B01D 53/56* (2006.01)
*B01D 53/86* (2006.01)
(52) U.S. Cl.
USPC ......... 423/239.1; 422/168; 422/177; 422/180

(58) Field of Classification Search
USPC .................. 423/239.1; 422/168, 177, 180
See application file for complete search history.

(56) References Cited

U.S. PATENT DOCUMENTS

| 3,467,492 A | 9/1969 | Newman |
| 6,056,928 A * | 5/2000 | Fetzer et al. .................. 423/235 |

(Continued)

FOREIGN PATENT DOCUMENTS

| EP | 2165756 | 3/2010 |
| JP | 55 031463 | 3/1980 |
| WO | WO 02/26355 | 4/2002 |
| WO | WO 2006/059506 | 6/2006 |

OTHER PUBLICATIONS

International Search Report mailed Apr. 19, 2010 for corresponding International Patent Application No. PCT/EP2010/000013.

(Continued)

*Primary Examiner* — Timothy Vanoy
(74) *Attorney, Agent, or Firm* — Swanson & Bratschun, LLC

(57) ABSTRACT

A device and method for the decomposition of laughing gas including a gas inlet for supplying a laughing-gas-bearing gas; a first heat-exchanger for the exchange of heat between an exhaust and the laughing-gas-bearing gas; a heating device for occasional heating of the laughing-gas-bearing gas and a fixed-bed reactor in which a catalyst is included in order to decompose the laughing gas. The device also includes a gas outlet, through which exhaust leaving the fixed-bed reactor can be taken away through the heat exchanger. The device may be used to implement a method where the catalyst for decomposition of laughing gas is maintained at temperatures below 800° C. and in which the fixed-bed reactor is arranged as an adiabatic reactor.

15 Claims, 1 Drawing Sheet

U.S. PATENT DOCUMENTS

| | | | |
|---|---|---|---|
| 2005/0281724 A1* | 12/2005 | Hotta et al. | 423/239.1 |
| 2008/0241034 A1* | 10/2008 | Schwefer et al. | 423/239.2 |
| 2010/0196238 A1* | 8/2010 | Fujiwara | 423/239.1 |
| 2010/0209325 A1* | 8/2010 | Schwefer et al. | 423/239.1 |
| 2010/0303699 A1* | 12/2010 | Sasaki | 423/239.2 |
| 2011/0117000 A1* | 5/2011 | Nakatani et al. | 423/239.1 |

OTHER PUBLICATIONS

English Translation of International Preliminary Report mailed Aug. 25, 2011 for corresponding International Patent Application No. PCT/EP2010/000013.

* cited by examiner

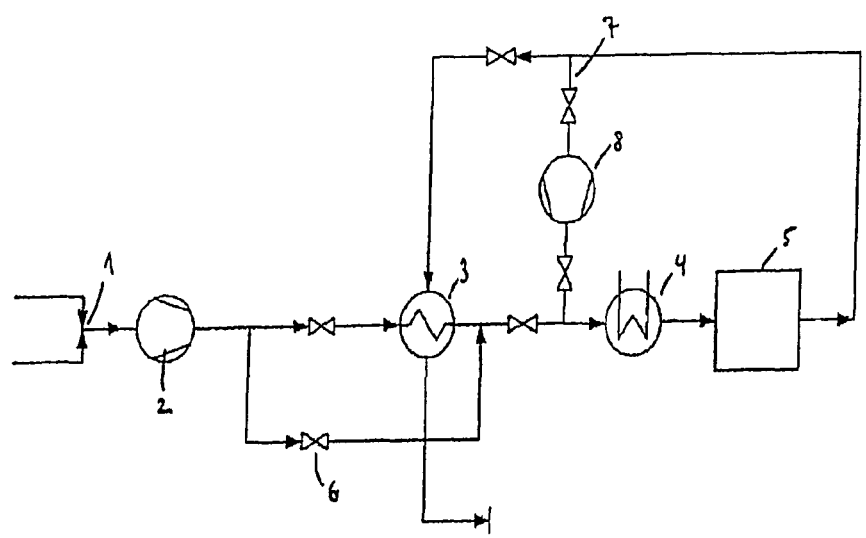

APPARATUS AND PROCESS FOR DECOMPOSING DINITROGEN MONOXIDE IN AN ADIABATIC FIXED BED REACTOR

RELATED APPLICATIONS

This application is a 35 U.S.C. §371 national phase application of PCT/EP2010/000013 (WO 2010/081642), filed on Jan. 5, 2010, entitled "APPARATUS AND PROCESS FOR DECOMPOSING DINITROGEN MONOXIDE IN AN ADIABATIC FIXED BED REACTOR", which application claims the benefit of German Patent Application Serial No. 102009004431.0, filed Jan. 13, 2009, which is incorporated herein by reference in its entirety.

The invention concerns a device and a method for decomposition of laughing gas ($N_2O$) in a fixed-bed reactor. Such a device and a corresponding method are known, for example, from the U.S. Pat. No. 7,235,222 B2, U.S. patent application 2006/0008401 A1, or WO 2006/059506 A1.

Nitrous oxide or laughing gas is a non-poisonous, colorless gas, which has long been used as an anesthetic or analgesic agent in combination with other substances. In addition, laughing gas also originates as a by-product in the manufacture of nitric acid or is used in organic syntheses. A problem exists in application as an anesthetic or analgesic agent, in that the laughing gas exhaled by the patient can be concentrated in the treatment space above the current maximally permissible workplace concentration and thus can also lead over a long time to an excessive burden for medical personnel.

In addition, increasing environmental awareness is driving the observation that laughing gas also markedly contributes to the greenhouse effect and to breakdown of the ozone layer.

Hence there is demand for a device and a method for the effective decomposition of laughing gas from various sources, be it from medical treatments, nitric-acid production, exhausts from various organic syntheses, in the cleaning/evacuating of gas cylinders, or from exhaust streams in the very manufacture of laughing gas, so that no laughing gas is released into the surroundings.

The patents and patent applications cited above deal with the recovery of laughing gas from medical applications and essentially propose collecting the laughing gas that accumulates in several treatment or operating spaces of a hospital complex and supplying a common catalytic treatment. Catalysts are preferably used for this which make decomposition of laughing gas possible at relatively low temperatures, that is, below 600° C. Different adsorbents in the catalytic treatment can be connected in series in order to separate out disruptive components such as sevofluorane, desfluorane, isofluorane, halothane, or other halogenated hydrocarbons.

In addition, the inventors of the present application have themselves proposed a device and a method for decomposition of laughing gas in the European patent application EP 08164753.9, which was not yet published at the time the present application was filed, which provides for transferring laughing gas accumulated directly on site in the treatment room for an individual patient, which saves the expensive collection of different streams of laughing gas within the hospital complex.

Other current, commercially available methods for laughing-gas removal are usually based on mainly thermal decomposition of laughing gas at more than 800° C.

More modern catalytic methods, which operate at temperatures below 600° C., have a common problem, namely that the decomposition of laughing gas is highly exothermic. This means that if the gas exhaled by the patient is subject to no further pre-processing for catalytic decomposition, then, due to the high laughing-gas concentration of up to 70%, such a highly exothermic reaction or heat development at the catalyst indicates that this is irreversibly damaging with a probability that is limiting to safety.

The current methods for removing laughing gas, as have been previously stated, hence have the common feature that the gas stream is diluted with another laughing-gas-free gas to a laughing-gas concentration of <5%. In addition, measures are accordingly provided for the catalyst to be able to operate isothermally, that is, for it to cool off or heat up.

In view of this prior art, it is a task of the invention to make available an improved device and an improved method for decomposition of laughing gas, which, without high energy consumption or costly, demanding materials, particularly temperature-stable substances, makes safe system operation possible.

The above task is resolved by a device according to claim 1 and a method according to claim 9. The dependent claims refer to further advantageous embodiments of the invention.

The invention is clarified in the following description with reference to the enclosed figure.

FIG. 1 shows a diagram of an embodiment by way of an example of a device for decomposition of laughing gas.

As may be seen in FIG. 1, the device according to the invention includes a gas inlet 1, for example a breathing mask, through which the laughing-gas-bearing gas enters. Reference number 2 denotes a blower to feed the inlet gas through the next component. This gas is conducted through a heat exchanging means or heat exchanger 3 and passes into a heating device 4. The gas, then passing on further, is fed to the reactor proper 5. The reactor 5, namely a fixed-bed reactor, is filled with a suitable catalyst, wherein a noble metal catalyst, in particular palladium or rhodium, in a suitable carrier is currently preferred. With regard to the actual form of the catalyst, no special restriction underlies the present invention. It is also possible to use a catalyst arrangement, as is shown, for example, in WO 2006/009453 A1.

The essentially laughing-gas-free gas leaving the reactor is passed through a gas line to the heat exchanger 3, where it gives up heat picked up through the exothermic reaction of the laughing-gas decomposition or through the heating element 4 to the laughing-gas-bearing inlet gas. Additional condensers can be provided as desired, so that the exhaust is given off to the surroundings with a temperature of about 40° C. or less.

According to the invention, a means of feedback 7, 8 can be provided in addition, for instance with a valve and a blower or compressor, with which it is possible to mix the gas leaving the catalyst into the laughing-gas-bearing inlet-gas stream, ahead of or behind the heating element, and thus lead to reducing the laughing-gas concentration in the inlet-gas stream and heat the inlet gas.

According to the invention, a bypass valve 6 is provided in addition, with which it is possible to pass the inlet gas in whole or in part to the heat exchanger 3. This is especially helpful if, due to the exothermic nature of the laughing-gas decomposition reaction, a greater rise in temperature is feared.

With a further bypass valve, not shown, it is also possible to pass the laughing-gas-bearing gas in whole or in part to the heating device.

As a possible embodiment example of the invention, the use of the device according to the invention is observed in the following in connection with the decomposition of the laughing gas in the breathing gas of a patient. Special difficulties arise here, since the gas stream exhaled contains up to 50%-70% laughing gas, wherein the remainder is mainly oxygen. In addition, smaller amounts of $CO_2$ are in the gas. A further difficulty results from the fact that the breathing gas and the laughing-gas-free gas mixed in for dilution, usually ambient air, are moist, depending on the application. The currently preferred catalysts show a strong dependence of laughing-gas decomposition temperature on the humidity of the gas, wherein the laughing-gas decomposition temperature in the moist gas is about 50° C. or more, some also going up to 200° C., over that in the dry gas.

Due to respiration, the gas accumulates in a discontinuous manner, depending on whether the patient is just exhaling or not. Also, it may be observed that with some treatment methods, the laughing-gas content of the anesthesia gas administered to the patient varies highly depending on time, so that sudden fluctuations between 0% and 70% can occur in the exhaled gas.

The device according to the invention is conceived as a mobile and compact unit to be used directly in or adjoining the treatment space, in which in particular the device according to the invention is also provided to be used in an ambulance. This requires that the device according to the invention should be self-sufficient, except for a power supply, that is, that it offer neither a water hook-up nor be supplied with other process streams (special diluting gases or means of reduction).

In order to protect medical personnel and other persons, it is absolutely required that the device for laughing-gas decomposition not acquire too high a temperature on the outside, so that touching it does not lead to burns. Hence the device is to be so insulated that the outside temperature does not rise above 40° C.

For similar reasons, the fact is also to be considered that the exhaust ultimately given off does not, insofar as possible, exceed this temperature limit.

In the procedure, it is required in addition that the device manage without measurement and control devices that are complicated to operate. It should also be suited for use in hospitals by personnel with less training or in a stressful situation, and incorrect operation of the device should be further ruled out.

For use in connection with medical gases, there are no special restrictions with regard to the catalyst used. In principle, noble-metal catalysts on a carrier material have proven suitable for laughing-gas reduction. Palladium, rhodium, platinum, ruthenium, and others, for example, number among the suitable noble metals. In particular, palladium and rhodium have proven to be suitable. Aluminum oxide, silicon oxide, and zeolite or mixtures thereof and others are worth considering for the carrier.

On the catalyst, the laughing gas reacts to form $N_2$ and $O_2$. Side reactions to other nitrogen oxides can be avoided. Laughing-gas decomposition is already being used with a dry gas below 200° C. in some catalyst systems, and it rises with the moisture in the gas to 400° C. or 450°. With the preferred catalyst system, significant laughing-gas reduction in the dry gas is already observed at a little above 150° C.

In the application in a hospital described above, the device in the simplest case is operated such that the exhaled gas of the patient is diluted taking into account the maximum concentration theoretically possible, so that a maximum laughing-gas concentration is set at <10%, preferably <5%, and particularly <2%. Any laughing-gas-free gas can be used for the dilution, for instance ambient air or even the exhaust of the catalyst itself.

In one preferred embodiment, if the maximum inlet concentration described above of 5% or 2% is permitted to be briefly exceeded, it is required here however that the temperature, either in the reactor or that of the exhaust, be monitored accordingly, so that upon exceeding a critical $T_{max}$, the inlet gas can be rapidly diluted further, in order to avoid passing through the reactor or damage to the system due to too great a rise in temperature.

For safety reasons, it is preferred in clinical use that the reaction proceed at essentially atmospheric pressure, in order not to deleteriously affect the patient's breathing, among other things. The use of a compressor should also be avoided, which would clearly increase the costs and the stress of noise. Nevertheless, in order to be able to conduct the gas safety through the reactor, a blower is provided at a suitable site.

The method according to the invention provides, firstly, for heating the laughing-gas-free gas to be processed by means of the heating element to a temperature at which the reaction starts at the catalyst. In the case described of breathing gas for a patient, this temperature is, with the currently preferred noble-metal catalysts, about 300-400° C. or slightly less. With a dry gas, such as occurs, for example, with the processing of residual gases when filling cylinders, or can be obtained by means of suitable drying of the breathing gas and diluting gas, an initial temperature below 300° C., preferably at 200° C., is chosen. The exact temperature at which the laughing-gas composition begins depends to a considerable extent on the catalyst system selected, and is to be determined in advance depending on this. As is known, the actual degree of conversion also depends on the temperature.

After a brief run-up phase, wherein the laughing-gas-bearing gas is heated ahead of the reactor, the exothermic nature of the laughing-gas decomposition reaction ensures that a considerable amount of heat is released in the reactor. Calculations show that the decomposition of 0.5% laughing gas is sufficient to heat the gas up about 13° C. The reaction in the reactor is run adiabatically, which means that the reactor is well encapsulated thermally with respect to the surroundings, so that it is heated up rapidly itself and can then be operated without further heat energy.

The exhaust of the reactor, which is essentially laughing-gas-free, is passed through an exhaust line to the heat exchanger, where it gives up its heat as completely as possible to the laughing-gas-bearing gas in front of the inlet to the reactor, better yet in front of the inlet to the heating element. If the laughing-gas-bearing gas is diluted by means of an essentially laughing-gas-free gas, the hot exhaust from the reactor can also be used for this dilution, which simplifies the form of the heat exchanger. This approach also allows the system to be operated with a relatively dry gas in applications in a hospital complex, since only the moisture contained in the breathing gas of the patient has to be removed, which is readily possible with an adsorbent, for instance a molecular sieve or by means of blue gel.

After a short time, the heating element can be turned off, and the reaction runs stably due only to the exothermic reaction of the laughing-gas decomposition at the catalyst. Too intense a rise in temperature is prevented by suitable dilution of the laughing-gas-bearing gas.

In one preferred embodiment of the method according to the invention, in a first phase, the laughing-gas-bearing gas is conducted, without dilution, through the heating element, so that only a small amount of gas has to be heated up. This gas, with a high laughing-gas concentration of up to 70%, is then conducted without delay through the catalyst, wherein it is intensely heated due to the high exothermic reaction of the exhaust and the catalyst.

In a second step, the laughing-gas-bearing gas is then increasingly diluted in front of the reactor, either as described, with the exhaust from the reactor or with ambient air, and the heating element is turned off.

With the approach described above, the start and run of the reaction is much faster than in known processes, which provide for thermal laughing-gas decomposition at 800° C. It is, then, particularly an advantage if it is considered that the device according to the invention is used in a treatment space in which longer breaks could also occur between individual treatments in which no laughing gas is administered. On the other hand, in just this situation, it is absolutely required, for instance in emergency operations, that the device for decomposition of laughing gas be made ready for use very rapidly, and a long warm-up phase is not practical, such as is required for conventional devices.

Aside from the applications described above in the field of medicine, the device according to the invention can also be used in other application areas, for example for decomposition of laughing gas when filling gas cylinders, if a partially empty cylinder has to be refurbished, and the gas still remaining in the cylinder has to be disposed of before refilling. Another use area occurs in connection with exhausts, for example in nitric-acid production or adipic acid production.

Furthermore, the device according to the invention and the method according to the invention are also used in current methods for manufacturing laughing gas, wherein exhaust streams with a still considerable portion of laughing gas which cannot by processed further, are to be regularly disposed of. In order to protect the environment, it is appropriate to also decompose the laughing gas in these exhaust streams before release into the surroundings.

In some applications, there are still more gaseous components in the laughing gas, which can in part disruptively affect the process. In particular, halogenated hydrocarbons, for example sevoflurane, desflurane, isoflurane, and halothane exist partially or completely in medical gas mixtures. These halogenated and partially-halogenated hydrocarbons number among the classical catalyst poisons and are irreversibly damaging to noble-metal catalysts, which would lead to a marked shortening of the service life of the catalysts. To avoid this damage, an appropriate adsorbent can be inserted ahead of the catalyst, which holds these components back. Of greater importance, the removal of halogenated hydrocarbons from the exhaust air is also for the protection of medical personnel.

In an embodiment of the invention, not further depicted, the device for decomposition of laughing gas exhibits several adiabatic fixed-bed reactions connected one after the other, wherein each contains a suitable catalyst, where condensers or heat exchangers can be provided between the individual fixed-bed reactors. The advantage of this arrangement is that severe overheating of the catalysts can be avoided.

A further advantage of this embodiment is that it is easy to arrange the individual catalysts in the adiabatic fixed-bed reactors as "cartridges", which can be replaced. With a total volume of 10 liters of catalyst, for example, it is possible to divide this up into three or four equally sized parts, and to replace these 2.5- to 3.5-liter-sized "cartridges" as needed. Since it follows from this that the first fixed-bed reactor is most highly charged, it is, for instance, possible, after a certain process period, to remove the catalyst from the first fixed-bed reactor and instead to move the catalyst from the second fixed-bed reactor forward. The catalyst from the third fixed-bed reactor is then placed in the second fixed-bed reactor and a new cartridge with new catalyst is inserted into the third and last fixed-bed reactor.

In the same way, any adsorbent provided for the removal of halogenated hydrocarbons is formed as a cartridge and replaced.

The invention is not limited to these examples described. The invention can be used everywhere where laughing gas is to be decomposed.

To attain the adiabatic operating state of the reactor, it can be insulated by any suitable measures. An especially advantageous insulation is the inclusion of the catalyst in a double-walled reactor vessel with vacuum insulation.

The device according to the invention is in addition provided, in an advantageous manner, with controls, which, depending on the temperature in the reactor, the temperature of the exhaust, the temperature of the inlet gas into the reactor, the extent of the dilution, the concentration of laughing gas, and/or time, which control the heating element, the dilution, and any bypass valves around the heating element and the heat exchanger.

In a further embodiment according to the invention, it is possible to dry the inlet gas before entry into the heating element, by means of suitable measures, a molecular sieve, for example. This has the advantage that the decomposition temperature at the catalyst is reduced considerably. If a dry gas is used for dilution, be it a special supply of gas or the dry exhaust from the catalyst, the drying device can be made small and compact. Diaphragm-based drying devices can also be used according to the invention.

If two or more adsorbents connected in parallel are provided, it is possible to use one of these adsorbents actively for drying the inlet gas, while another one is connected to the exhaust stream, so that the hot exhaust continues to carry the adsorbed water out and regenerates the adsorbent for the next cycle. A plurality of adsorbents facilitates time-set cycles.

In another preferred embodiment of the method according to the invention, the inlet gas is dried at the start with a small, compact dryer and conducted through a heating element, which can be small as well, since a high start-up temperature is not required in the dry gas; a "cold start" is also facilitated. After reaching the normal operating temperature of the catalyst, 400° C. for instance, operation can be then carried out without drying or additional heating.

For further diminution of the dryer or the heating element and of energy consumption, it is possible at the start to use only a slightly or undiluted breathing gas for the patient and to switch on the dilution later, if needed.

The heating element is not limited to an electric heating element, although this is preferred. Alternatively, the laughing-gas-bearing inlet gas can also be heated by other means, for example an element heated by a chemical reaction. For use in an ambulance, the heat of the engine can also be used for the heating.

The invention claimed is:

1. A device for decomposition of laughing gas comprising:
    a gas inlet (1) for supplying a laughing-gas-bearing gas;
    a first heat-exchanger means (3) for the exchange of heat between an exhaust and the laughing-gas-bearing gas;
    a heating device (4) for occasional heating of the laughing-gas-bearing gas;
    a fixed-bed reactor (5), in which a catalyst is included in order to decompose the laughing gas in the laughing-gas-bearing gas;
    a gas outlet, through which the exhaust leaving the fixed-bed reactor can be taken away through the heat exchanger;
    characterized in that
    the catalyst for decomposition of laughing gas is suitable at temperatures below 800° C.; and
    in which the fixed-bed reactor (5) is arranged as an adiabatic reactor.

2. The device according to claim 1, characterized in that a feedback means (7, 8) is provided in order to mix at least one part of the exhaust with the laughing-gas-bearing gas ahead of the fixed-bed reactor (5).

3. The device according to claim 2, characterized in that the feedback means (7, 8) is arranged in order to mix one part of the exhaust with the laughing-gas-bearing gas ahead of the heating device (4).

4. The device according to claim 1 characterized in that a first control means is provided in order to control the operation of the heating device (4) as a function of the temperature of the laughing-gas-bearing gas, the temperature of the fixed-bed reactor (5), the temperature of the exhaust, the extent of the exhaust feedback, the laughing-gas concentration, and/or time.

5. The device according to claim 1, characterized in that a bypass valve (6) is provided in order to at least occasionally detour around the heat-exchanger means (3).

6. The device according to claim 5, characterized in that a second control means is provided in order to control the bypass valve (6) as a function of the temperature of the laughing-gas-bearing gas, the temperature of the fixed-bed reactor (5), the temperature of the exhaust, the extent of the exhaust feedback, the laughing-gas concentration, and/or time.

7. The device according to claim 1, characterized in that a diluting agent is provided in order to dilute the laughing-gas-bearing gas with another essentially laughing-gas-free gas.

8. A device according to claim 1 characterized in that a plurality of adiabatic, fixed-bed reactors (5) is provided in series, in which respective heat exchangers or condensers are optionally introduced between the individual fixed-bed reactors (5).

9. A method for decomposition of laughing gas comprising:
   a step for supplying a laughing-gas-bearing gas;
   a heat-exchange step for heat exchange between an exhaust and the laughing-gas-bearing gas;
   a heating step for occasional heating of the laughing-gas-bearing gas;
   a reaction step for the catalytic decomposition of the laughing gas in the laughing-gas-bearing gas in a fixed-bed reactor (5);
   a step for taking the exhaust away from the fixed-bed reactor (5) through the heat exchanger;
   characterized in that
   the reaction step begins at a temperature below 800° C., and the reaction takes place under adiabatic conditions.

10. The method according to claim 9, characterized in that the laughing-gas-bearing gas is mixed with at least a part of the exhaust ahead of the fixed-bed reactor (5).

11. The method according to claim 10, characterized in that the mixing occurs before the heating step.

12. The method according to claim 9 characterized in that the heating step is controlled as a function of the temperature of the laughing-gas-bearing gas, the temperature of the fixed-bed reactor (5), the temperature of the exhaust, the extent of the exhaust feedback, the laughing-gas concentration, and/or time.

13. The method according to claim 9 characterized in that the laughing-gas-bearing gas is occasionally conducted past, entirely or partially, in a bypass valve (6) at the heat-exchange step.

14. The method according to claim 13, characterized in that the bypass valve (6) is controlled as a function of the temperature of the laughing-gas-bearing gas, the temperature of the fixed-bed reactor (5), the temperature of the exhaust, the extent of the exhaust feedback, the laughing-gas concentration, or time.

15. The method according to claim 9 characterized in that the laughing-gas-bearing gas is diluted with another essentially laughing-gas-free gas.

* * * * *